_United States Patent_ [19]

Rule et al.

[11] Patent Number: 4,806,697

[45] Date of Patent: Feb. 21, 1989

[54] SELECTIVE LIQUID PHASE DISPROPORTIONATION CATALYSTS FOR IODOAROMATICS

[75] Inventors: Mark Rule; Gerald C. Tustin, both of Kingsport, Tenn.

[73] Assignee: Eastman Kodak Company, Rochester, N.Y.

[21] Appl. No.: 29,949

[22] Filed: Mar. 25, 1987

[51] Int. Cl.$^4$ .................. C07C 17/12; C07C 25/00
[52] U.S. Cl. .................. 570/202; 570/203; 570/208
[58] Field of Search ............... 570/202, 203, 206, 208

[56] References Cited

U.S. PATENT DOCUMENTS

| | | | |
|---|---|---|---|
| 3,363,010 | 1/1968 | Schwarzenbek | 570/203 |
| 4,368,339 | 1/1983 | Tada et al. | 570/202 |

FOREIGN PATENT DOCUMENTS

| | | | |
|---|---|---|---|
| 0046665 | 3/1982 | European Pat. Off. | 570/202 |
| 0062261 | 10/1982 | European Pat. Off. | 570/202 |
| 0181790 | 5/1986 | European Pat. Off. | 570/203 |
| 0183579 | 6/1986 | European Pat. Off. | 570/203 |
| 0077631 | 5/1982 | Japan | 570/203 |
| 0144330 | 8/1983 | Japan | 570/202 |
| 88/02358 | 4/1988 | World Int. Prop. O. | 570/203 |

_Primary Examiner_—Werren B. Lone
_Attorney, Agent, or Firm_—Charles R. Martin; W. P. Heath, Jr.

[57] ABSTRACT

The invention relates to a process for isomerizing iodoaromatic compounds over a non-acidic zeolite catalyst in the liquid or gas phase in the presence of a source of iodine.

22 Claims, No Drawings

SELECTIVE LIQUID PHASE DISPROPORTIONATION CATALYSTS FOR IODOAROMATICS

BACKGROUND OF THE INVENTION

1. Field of the Invention

The present invention relates to a process for selectively isomerizing iodoaromatic compounds, especially for converting 2-iodonaphthalene to mixtures of naphthalene, iodonaphthalenes, and 2,6-diiodonaphthalene.

2. Discussion of Background

It has long been desired to be able to derivatize aromatic compounds and in particular condensed ring aromatic compounds in commercially attractive quantities since many of these compounds possess properties which would fill long sought needs. In particular, the compound 2,6-naphthalene dicarboxylic acid or its esters is particularly desired for use in the manufacture of polyesters which would have excellent barrier properties when fabricated into films, bottles or coatings. However, known techniques for producing 2,6-naphthalene dicarboxylic acid and esters are very expensive and impractical for commercial exploitation.

3. Description of the Prior Art

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Pat. No. 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are idoic acid, sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese Patent Publication 81/77631 in the absence of any oxidizing agent.

Ishida and Chono in Japanese Kokai No. 59/219241 have suggested a technique for oxyiodinating benzene over very acidic zeolite catalyst having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

OTHER INFORMATION

Paparatto and Saetti disclosed in European Patent Applications Nos. 181,790 and 183,579 techniques for oxyiodination of benzene over zeolite catalysts. European Patent Application No. 181,790 suggests the use of ZSM-5 and ZSM-11 type zeolites which have been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in non-acid form. According to No. 183,579 the X or Y zeolites have to be used in the form exchanged with monovalent, bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

RELATED APPLICATIONS

Copending Applications Ser. Nos. 912,806, filed Sept. 29, 1986, 029,959 filed Mar. 25, 1987, and 029,899 filed Mar. 25, 1987 disclose techniques for iodinating aromatic compounds over non-acid catalysts. The selectivities of these techniques is improved by conducting the techniques at comparatively low temperatures on the order of from about 100° C.–250° C. and using an oxidation catalyst.

There is a need to isomerize the iodoaromatic compounds produced in these processes since undesired isomers are frequently produced. U.S. Patent Application Ser. No. 029,899 filed Mar. 25, 1987 discloses a process for isomerizing or transiodinating iodoarmoatic compounds in the presence of a non-acid catalyst. This process requires the vaporization of the iodoaromatic compound and therefore requires a substantial input of energy. Consequently, this process works well only with relatively volatile iodoaromatic compounds. Polynuclear iodoaromatic compounds frequently have high boiling points and are difficult to vaporize without concomittent decomposition. Vaporization of these compounds requires a substantial input of heat energy.

U.S. Patent Application Ser. No. 029,956 filed Mar. 25, 1987 discloses a process for the liquid phase isomerization of iodoaromatic compounds in the presence of an acidic catalyst. Although isomerization using this process occurs at lower temperatures, the isomerization reaction is largely non-selective.

The above-referenced U.S. patent applications are herein incorporated by reference.

Liquid phase isomerization reactions which employ selective catalysts would allow for the more efficient production of specific iodoaromatic compounds, and are therefore of considerable economic interest. There is presently no effective means for this selective isomerization.

Accordingly, need exists for a process by which undesired iodoaromatic isomers can be easily and economically isomerized to desired isomeric products.

A further need exists for a process by which undesired iodoaromatic isomers can be selectively isomerized at relatively low temperatures and in a liquid phase without decomposition of the isomers.

A need also exists for a process by which 2-iodonaphthalene can be selectively isomerized in the liquid or gas phase to mixtures of naphthalene, iodonaphthalenes, and 2,6-diiodonaphthalene, without decomposition of the isomers.

BRIEF DESCRIPTION OF THE INVENTION

Accordingly, one object of the present invention comprises a technique for isomerizing an iodoaromatic compound over a non-acidic catalyst to effect isomerization to desired isomers.

A further object of the present invention comprises a technique for the liquid or gas phase isomerization of 2-iodonaphthalene to a mixture of naphthalene, iodonaphthalenes, and 2,6-diiodonaphthalene, over a non-acidic catalyst.

Another object of the invention comprises a method for oxyiodinating an aromatic compound over a non-acid catalyst and isomerizing the iodinated product over a non-acid catalyst.

These objects and further objects of the present invention which will become apparent from the following disclosure have been attained by the process of the present invention which comprises contacting an iodoaromatic compound with a non-acidic zeolite catalyst in the liquid or gas phase in the presence of a source of iodine to effect isomerization.

DESCRIPTION OF THE PREFERRED EMBODIMENTS

The term "isomerization" as used herein means intra- or intermolecular iodine transfer.

The iodoaromatic compounds utilized in this invention may be prepared by any suitable technique, such as described above.

It is quite surprising that the isomerization reaction of the present invention works at all given the fact that the liquid phase isomerization reaction of Application Ser. No. 029,956 filed Mar. 25, 1987 requires the use of an acidic catalyst and yields a thermodynamic mixture of isomers; in contrast, the present invention comprises the use of a non-acidic catalyst and transiodinates with a surprising degree of selectivity. The efficiency of the present isomerization reaction is even more surprising in view of the fact that the zeolites utilized are inactive for the isomerization of aromatics by themselves, but are quite effective upon activation. One suitable method for activation is to add small amounts of iodine. The catalysts utilized in the present process can be generally characterized as being y-type zeolites which contain alkali or alkaline earth metals. Y-type zeolites are characterized as faujasite-type zeolites with a silicon to aluminum ratio greater than 1.5.

Most of the commercially available zeolites are prepared in the sodium form. Different metal counterions are easily introduced into the zeolite by a simple ion exchange process which is well known to those skilled in the art. This is generally accomplished by contacting the zeolite with an aqueous salt solution of the desired counterion. The period of time over which the contact is conducted and the number of times the ion exchange process is performed is dependent upon the degree of replacement which is desired. Thus, one beginning with the zeolite in the sodium form may ion exchange this material with another counterion to partially or substantially completely replace the sodium ion with a different metal counterion. The particular counterion which is employed has an effect upon the product composition. Suitable counterions are alkali or alkaline earth cations. Preferred counterions are sodium, potassium, rubidium and cesium ions. Particularly preferred are potassium ions. The use of potassium counterions particularly favors the production of 2,6-diiodonaphthalene, which is a desirable intermediate for the manufacture of a number of compounds, especially 2,6-naphthalenedicarboxylic acid and its derivatives. Specific Y-type zeolite catalysts which are preferred include the sodium zeolite LZY-52 and the potassium zeolite obtained by exchanging LZY-52 with KCl followed by calcining.

Catalyst activity (rate) and selectivity is dependent on the specific type of catalyst used. Alkaline earth and sodium Y-type zeolites are the most active catalysts followed by potassium, rubidium, and cesium Y-type zeolites. The potassium, rubidium and cesium Y-type zeolites are the most selective followed by the sodium Y-type zeolites and the alkaline-earth exchanged Y-type zeolites.

The isomerization reaction works for single ring iodoaromatics and polycyclic iodoaromatic compounds, including substituted and unsubstituted iodoaromatics. Suitable aromatic compounds include hydrocarbon aromatics, oxygen-containing aromatics and sulfur-containing aromatics. Typical hydrocarbon aromatics include benzene, biphenyl, naphthalene and anthracene. Typical sulfur-containing aromatics include thiophene and benzothiphene. Typical oxygen-containing aromatics include furan and benzofuran. Substituted aromatics include compounds such as sulfones, diaryl ethers, diaryl carbonyls, diaryl sulfides and the like. Aromatic compounds substituted by alkyl groups are generally not preferred for utilization in the present technique. One generally obtains products which are iodinated not only on the ring but also on the side chains. Thus, while alkyl substituted aromatics can be utilized in the present technique, their use is not preferred. Preferred reactants for the isomerization reaction are iodobenzenes, iodobiphenyls and iodonaphthalenes. A particularly preferred reactant is 2-iodonaphthalene.

The reaction rate is temperature dependent and the rate decreases as the temperature decreases. For iodobenzenes, iodobiphenyls or iodonaphthalenes, the preferred temperatures are between about 150° C. and about 300° C. Similar temperature ranges would be used for other iodinated aromatic compounds. Preferred reaction temperatures are between about 200° C. and 275° C. The use of slightly higher or lower temperatures is a matter of choice depending on the nature of the catalyst and iodoaromatic compounds to be isomerized. The isomerization of the single ring compounds may require somewhat higher temperatures than isomerizations involving condensed ring aromatics. For isomerization of 2-iodonaphthalene, the specifically preferred temperatures are between 200° and 250° C. The upper limit of the temperature range is practically determined by the temperature at which decomposition of the iodoaromatic compound begins to occur. The use of relatively lower temperatures is preferred since the decomposition of the iodoaromatic compounds is minimized.

The isomerization reaction is preferably run in the absence of solvent, and can be run in the liquid or gas phase. However, the reaction will proceed equally well in the presence of suitable inert organic solvents, i.e., those solvents which are not susceptible to iodination under the conditions employed in the isomerization reaction. Suitable inert solvents include alkanes and cycloalkanes, such as hexane, heptane, octane, cyclohexane, decalin, etc.

The pressure at which the process is conducted is not critical and can range from subatmospheric to superatmospheric. The utilization of elevated pressures may be useful when the process is operated in the presence of solvent, particularly solvents with relatively low boiling points. The use of higher pressures allows the isomerization reaction to be run at elevated temperatures, i.e., temperatures above boiling point of the solvent. In general, pressures from atmospheric to about 600 psig have proven satisfactory although higher or lower pressures can be utilized.

The isomerization reaction can be run in the presence of molecular oxygen or air and therefore, the starting materials and solvents do not have to be degassed prior to reaction.

The isomerization of iodoaromatic compounds in this fashion is quite surprising and unexpected, since the isomerization of haloaromatic compounds is considered to be a difficult process, requiring a strongly acidic catalyst and long reaction times. For example, see Olah, in *Journal of Organic Chemistry*, 27, 3469 (1962).

While not being bound to any particular theory, it is believed that when activated by iodine, the iodine disproportionates on the catalyst to iodide and a species of the type IOAl, which is the catalytically active species. The catalytically active species then transfers iodine to an aromatic compound and generates HOAl, which can abstract iodine from another iodoaromatic molecule, regenerating IOAl. The net effect of this reaction is the redistribution of iodide among the aromatic species present. Because of the structural constraints of the zeolite, certain isomers are more readily transiodinated than other. Among the iodonaphthalenes, the preferred reactant is 2-iodonaphthalene and the iodide is then redistributed to produce a substantial quantity of 2,6-diiodonaphthalene and naphthalene. Although other iodonaphthalene isomers are also formed, they are produced at substantially slower rates. Similarly, 4-iodobiphenyl disproportionates selectively to biphenyl and 4,4'-diiodobiphenyl.

Iodine may be added to the reaction in the form of $I_2$ or HI as well as in the form of alkyl iodides. The preferred form of iodine is $I_2$. The amount of iodine added to the reaction is a matter of choice depending on the reaction conditions. However, the reaction will proceed substantially well when only a catalytic amount of iodine is added. The catalysts may also be activated by the addition of other halogens.

The isomerization reaction can be operated as a continuous process or can be carried out as batch or semi-batch processes if desired and can be coupled to any suitable iodination reaction. A preferred embodiment is to couple the isomerization reaction with an oxyiodination reaction, as described in Application Ser. No. 912,806. When the oxyiodination reaction is performed as a continuous process, the isomerization reaction can be performed continuously by accepting the reaction product from the oxyiodination reaction. One or more desired products may be isolated prior to and/or after the isomerization reaction. The remaining effluents from the isomerization reaction can then be recycled and again passed through the isomerization or oxyiodination process. It is also possible to pass the effluent from the oxyiodination reaction through several isomerization catalysts beds isolating one or more desired products after each isomerization reaction. These isomerization beds may contain the same or different isomerization catalysts, with similar or differing activities or selectivities.

The effluent from the isomerization reaction can also be recycled to the oxyiodination and/or isomerization catalysts. In a particularly preferred embodiment, iodine, oxygen and the aromatic starting compounds are first passed through the oxyiodination catalyst. The desired isomeric products can be optionally separated and drawn off at this point using conventional means which are well known. The remaining effluent can then be passed through the isomerization catalyst followed by a separation to remove the desired product. Uniodinated compounds and undesired isomers can then be separated, with the uniodinated compounds being recycled to the oxyiodination catalyst and the undesired isomers recycled to the isomerization catalysts. In addition to the present catalysts, isomerization catalysts which are unselective, such as those disclosed in U.S. Application Ser. No. 029,956, filed Mar. 25, 1987 may also be used. These unselective catalysts may be used alone or in addition to the selective isomerization catalysts to achieve even higher efficiencies. The sequence of isomerization reactions is determined by the specific reactants and conditions involved. If the separation of undesired isomers and uniodinated compounds is not desired or technically feasible, the unseparated mixture can be recycled to either the oxyiodination or isomerization catalysts. The method of recycling is a matter of choice and is dependent on the reactivity of the compounds, nature of the catalyst, reaction conditions and the ability to separate the various products effectively. When operated in this embodiment, there is very little loss of reactant materials and the products can be recycled continuously to produce any one of a number of desired isomers. Preferably, moniodinated and diiodinated products are produced.

Another possibility is to operate the process batchwise. The isomerization reaction can be run in conjunction with an oxyiodination reaction or it can be operated as a stand-alone process. When operated with an oxyiodination process, the oxyiodination reaction is performed, the desired product separated and removed, and the undesired isomers and unreacted compounds collected. The collected material can then be subsequently passed over the isomerization catalyst bed to effect isomerization. Another embodiment of this invention is to iodonate an aromatic species by transferring iodide from another species, such as iodinating naphthalene by transferring iodide from iodobenzene.

Obviously, it is possible to combine various aspects of these different embodiments to achieve the desired products and economic efficiency. For example, it is possible to perform the oxiodination and isomerization reactions and then subsequently pass some portion of the effluent to a second or third isomerization catalyst bed to further redistribute the iodine among the aromatic species. This flexibility is important since it allows one to produce and isolate a number of different iodoaromatic compounds. All embodiments of the invention can be performed in combination or alone and continuously, or as batch or semi-batch processes.

If the isomerization catalyst requires regeneration due to the deposition of carbon on the catalyst, the catalyst can be readily reactivated by passing air or oxygen over the catalyst for several hours at elevated temperatures.

The following examples are presented to illustrate the present invention but are not intended in any way to limit the scope of the invention which is defined by the appended claims.

EXAMPLE 1

In the examples below the stated amounts of reactants and catalyst were mixed in a reaction tube fitted with a ground glass joint and stopper and placed in a heat block at the desired temperature. Samples were removed periodically for analysis for gas chromatography. The analysis are reported in mole %. Some naphthalene was lost from the reaction mixture by evaporation.

---

1. 0.2 grams K—Y (LZY-52 exchanged with KCl and calcined)
   0.5 grams monoiodonaphthalenes (78% 2-iodo, 22% 1-iodo)
   0.02 grams I2
   200 deg C.
   After 90 minutes, the product contained 3.2% naphthalene, 68.4% 2-iodonaphthalene, 18.6% 1-iodonaphthalene, and 9.75% diiodonaphthalenes, with the 2,6 isomer constituting 57.4% of the diiodonaphthalenes and with a 2,6/2,7 ratio of 4.6.
2. 0.2 grams K—Y (as in Example 1)
   0.5 grams monoiodonaphthalenes (as in Example 1)
   0.02 grams I2
   230 deg C.
   After 90 minutes, the reaction product contained 8.7% naphthalene, 54.8% 2-iodonaphthalene, 18.0% 1-iodonaphthalene, and 18.5% diiodonaphthalenes, with the 2,6 isomer constituting 75.7% of the diiodonaphthalenes, and with a 2,6/2,7 ratio of 9.6.
3. 0.2 grams Na—Y (LZY-52)
   0.5 grams monoiodonaphthalenes (as in Example 1)
   0.02 grams I2
   200 deg C.
   After 90 minutes, the reaction product contained 4.7% naphthalene, 60.6% 2-iodonaphthalene, 19.5% 1-iodonaphthalene, and 15.2% diiodonaphthalenes. The 2,6 isomer constituted 45.3% of the diiodonaphthalenes with a 2,6/2,7 ratio of 2.13.
4. 0.2 grams Ca—Y (prepared by CaCl2 exchange on LZY-52)
   0.5 grams monoiodonaphthalenes (as in Example 1)
   0.02 grams I2
   200 deg C.
   After 90 minutes, the reaction product contained 7.9% naphthalene, 55.2% 2-iodonaphthalene, 17.8% 1-iodonaphthalene, and 19.1% diiodonaphthalenes. The 2,6 isomer constituted 39% of the diiodonaphthalenes with a 2,6/2,7 ratio of 1.9.
5. 0.47 grams K—Y
   1.0 grams 4-iodobiphenyl
   0.02 grams I2
   210 deg C.
   After 3.5 hours, the reaction product contained 9.2% biphenyl, 0.3% 3-iodobiphenyl, 72.0% 4-iodobiphenyl, 17.0% 4,4'-diiodobiphenyl, and 1.4% other diiodobiphenyls.
6. 0.43 grams K—Y
   1.0 grams p-iodobenzene
   0.02 grams I2
   210 deg C.
   After 3.5 hours, the reaction product contained 87.2% iodobenzene, 10.4% p-diiodobenzene, 1.4% m-diiodobenzene and 0.8% o-diiodobenzene.

---

Obviously, numerous modifications and variations of the present invention are possible in light of the above teachings, and that the invention may be practiced otherwise than as specifically described herein.

While the invention has been described in detail with particular reference to preferred embodiments thereof, it will be understood that variations and modifications can be effected within the spirit and scope of the invention.

We claim:

1. A process of isomerizing an iodoaromatic compound, said process comprising the step of:
   contacting a mono-, di-, or tri-iodoaromatic compound selected from the group consisting of benzene, biphenyl, naphthalene, anthracene, thiophene, benzothiophene, furan and benzofuran with a non-acidic zeolite catalyst in the liquid or gas phase in the presence of iodine, whereby the iodine present in said iodoaromatic compound is redistributed among the molecules of said iodoaromatic compound to form an isomerized product.
2. The process of claim 1 wherein said iodoaromatic compound is an iodobenzene, iodobiphenyl or an iodonaphthalene.
3. The process of claim 1 wherein said contacting step is conducted in the presence of $I_2$, HI or alkyl iodides.
4. The process of claim 1 wherein said contacting step occurs at temperatures between about 150° C. and 300° C.
5. The process of claim 4 wherein said contacting step occurs at temperatures between about 200° C. and 250° C.
6. The process of claim 2 wherein said iodonaphthalene is 2-iodonaphthalene.
7. The process of claim 1 wherein said catalyst is Y-type zeolite containing alkali or alkaline earth cations.
8. The process of claim 7 wherein said Y-type zeolite contains potassium cations.
9. The process of claim 1 wherein said iodoaromatic compound is a product resulting from an oxyiodination reaction.
10. The process of claim 9 wherein:
    (a) said contacting step is performed continuously and
    (b) at least a portion of the product of said contacting step is recycled to the beginning of said contacting step.
11. A process for iodinating an aromatic compound, the process comprising the steps of:
    (a) reacting iodine and an aromatic compound selected from the group consisting of benzene, biphenyl, naphthalene, anthracene, thiophene, benzothiophene, furan and benzofuran in the presence of oxygen over a non-acid zeolite catalyst to produce a mono-, di-, or tri-iodoaromatic compound; and
    (b) contacting said iodoaromatic compound with a non-acidic zeolite catalyst in the liquid or gas phase in the presence of iodine, whereby the iodine present in said iodoaromatic compound is redistributed among the molecules of said iodoaromatic compound to form an isomerized product.
12. A process of claim 11 wherein said non-acidic zeolite is a Y-type zeolite containing alkali or alkaline earth cations.
13. The process of claim 11 wherein said aromatic compound is benzene, naphthalene or biphenyl.
14. The process of claim 11, wherein said iodoaromatic compound is an iodonaphthalene.
15. The process of claim 14 wherein said iodonaphthalene is 2-iodonaphthalene.
16. The process of claim 11 wherein said non-acid catalyst contains an effective amount of an oxidation catalyst.
17. The process of claim 11 wherein said contacting step is conducted in the presence of $I_2$, HI or alkyl iodides.
18. The process of claim 11 wherein said contacting step occurs at temperatures between about 150° C. and 300° C.
19. The process of claim 18 wherein said contacting step occurs at temperatures between about 200° C. and 250° C.

20. The process of claim 14 wherein said iodonaphthalene is 2-iodonaphthalene.

21. The process of claim 12 wherein said Y-type zeolite contains potassium cations.

22. The process of claim 11 wherein:

(a) said contacting step is performed continuously and
(b) at least a portion of the product of said contacting step is recycled to the beginning of said contacting step.

* * * * *